United States Patent
Kolter et al.

(10) Patent No.: US 8,951,569 B2
(45) Date of Patent: Feb. 10, 2015

(54) PELLETS COATED WITH COATINGS CONTAINING ACTIVE SUBSTANCES

(75) Inventors: Karl Kolter, Limburgerhof (DE); Dejan Djuric, Mannheim (DE); Stefan Fischer, Freinsheim (DE); Matthias Karl, Mannheim (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 13/496,533

(22) PCT Filed: Sep. 13, 2010

(86) PCT No.: PCT/EP2010/063393
§ 371 (c)(1),
(2), (4) Date: Mar. 16, 2012

(87) PCT Pub. No.: WO2011/032916
PCT Pub. Date: Mar. 24, 2011

(65) Prior Publication Data
US 2012/0183623 A1    Jul. 19, 2012

(30) Foreign Application Priority Data
Sep. 17, 2009    (EP) .................................. 09170553

(51) Int. Cl.
| A61K 9/16 | (2006.01) |
| C08F 226/06 | (2006.01) |
| C08F 283/06 | (2006.01) |
| C08L 1/02 | (2006.01) |
| C08L 5/00 | (2006.01) |
| C09D 151/08 | (2006.01) |
| C09D 171/02 | (2006.01) |
| C08F 218/08 | (2006.01) |
| C08L 51/08 | (2006.01) |

(52) U.S. Cl.
CPC ............. *A61K 9/1676* (2013.01); *A61K 9/1641* (2013.01); *C08F 226/06* (2013.01); *C08F 283/06* (2013.01); *C08L 1/02* (2013.01); *C08L 5/00* (2013.01); *C09D 151/08* (2013.01); *C09D 171/02* (2013.01); *C08F 218/08* (2013.01); *C08L 51/08* (2013.01)
USPC ........................................ 424/497; 427/2.15

(58) Field of Classification Search
CPC . A61K 9/1641; A61K 9/1676; C09D 171/02; C09D 151/08; C08L 5/00; C08L 1/02; C08L 51/08; C08F 283/06; C08F 226/06; C08F 218/08
USPC ........................................ 424/497; 427/2.15
See application file for complete search history.

(56) References Cited

U.S. PATENT DOCUMENTS

| 5,840,881 A * | 11/1998 | Uda et al. ........................ 536/46 |
| 6,867,262 B1 | 3/2005 | Angel et al. |
| 2003/0032879 A1 * | 2/2003 | Quay ............................. 600/437 |
| 2003/0077297 A1 * | 4/2003 | Chen et al. .................... 424/400 |
| 2004/0043070 A1 * | 3/2004 | Ayres ............................ 424/471 |
| 2006/0003008 A1 * | 1/2006 | Gibson et al. ................. 424/486 |
| 2007/0292523 A1 * | 12/2007 | Moodley et al. .............. 424/497 |
| 2008/0293828 A1 * | 11/2008 | Bouillo et al. ............. 514/772.3 |
| 2010/0204425 A1 | 8/2010 | Mertoglu et al. |
| 2011/0178183 A1 | 7/2011 | Meyer-Boehm et al. |
| 2011/0195118 A1 | 8/2011 | Kolter et al. |
| 2011/0256193 A1 | 10/2011 | Meyer-Bohm et al. |
| 2012/0022079 A1 | 1/2012 | Meyer-Böehm et al. |

FOREIGN PATENT DOCUMENTS

| DE | 19935063 | 2/2001 |
| JP | 2003-522097 | 7/1993 |
| JP | 07-126153 | 5/1995 |
| JP | 2007-506786 | 3/2007 |
| WO | WO-99/40943 | 8/1999 |
| WO | WO-2005/072079 | 8/2005 |
| WO | WO 2006037344 A1 * | 4/2006 |
| WO | WO-2007/051743 | 5/2007 |
| WO | WO-2008/027993 | 3/2008 |
| WO | WO-2009/013202 | 1/2009 |
| WO | WO-2010/034688 | 4/2010 |
| WO | WO-2010/040686 | 4/2010 |
| WO | WO-2010/072573 | 7/2010 |
| WO | WO-2010/112489 | 10/2010 |
| WO | WO-2010/130728 | 11/2010 |

OTHER PUBLICATIONS

Chen et al. (Enhanced bioavailability of the poorly water-soluble drug fenofibrate by using liposomes containing a bile salt, Int J Pharm (Jul. 6, 2009) 376 (1-2): 153-160 [Abs. Downloaded Jun. 4, 2012] [Retrieved from internet <URL: http://www.ncbi.nlm.nih.gov/pubmed/19394416 >]), 1 page.*
Verreck et al., The Use of Three Different Solid Dispersion Formulations—Melt Extrusion, Film-Coated Beads, and a Glass Thermoplastic System—To Improve the Bioavailability of a Novel Microsomal Triglyceride Transfer Protein Inhibitor, Journal of Pharmaceutical Sciences (May 2004), vol. 93, No. 5, pp. 1217-1228 (12 pages).*
Karanth et al., Industrially Feasible Alternative Approaches in the Manufacture of Solid Dispersions: A Technical Report, AAPS Pharm SciTech (2006), 7(4) Article 87, pp. E1-E7 (7 pages).*
Beck et al., Nanoparticle-coated microparticles: preparation and characterization, J. Microencapsulation (Aug. 2004), vol. 21, No. 5, pp. 499-512. (15 pages).*
International Search Report for PCT/EP2010/063393, mailed on Dec. 2, 2010, 2 pages.

* cited by examiner

Primary Examiner — Jason Sims
Assistant Examiner — Miriam A Levin
(74) Attorney, Agent, or Firm — Servilla Whitney LLC

(57) ABSTRACT

Formulations of sparingly water-soluble active ingredients, consisting of carrier particles provided with active ingredient-containing coatings, the sparingly soluble active ingredients being embedded in coatings composed of amphiphilic copolymers.

14 Claims, No Drawings

PELLETS COATED WITH COATINGS CONTAINING ACTIVE SUBSTANCES

CROSS-REFERENCE TO RELATED APPLICATIONS

This application is the national stage entry of PCT/EP2010/063393, filed on Sep. 13, 2010, which claims priority to European Patent Application No. EP 09170553.3, filed on Sep. 17, 2009, both of which are incorporated herein by reference in their entireties.

BACKGROUND

In the production of homogeneous formulations, especially of biologically active substances, the solubilization of hydrophobic, i.e. sparingly water-soluble, substances has gained very great practical significance.

Solubilization is understood to mean the solubilizing of substances which are sparingly soluble or insoluble in a particular solvent, especially water, by means of interface-active compounds, the solubilizers. Such solubilizers are capable of converting sparingly water-soluble or water-insoluble substances to clear, at worst opalescent aqueous solutions, without the chemical structure of these substances undergoing any change in the process.

Many known polymeric solubilizers have the disadvantage that they do not form stable solid solutions. Moreover, they still leave room for improvement as far as solubilization in aqueous systems is concerned. With regard to processibility too, some of the known solubilizers have disadvantages owing to their tendency to tackiness, since they are not sufficiently free-flowing powders.

DE-A 199 350 63 discloses polyalkylene oxide-containing graft polymers based on vinyllactams and vinyl acetate, and the use thereof as gas hydrate inhibitors.

WO 2007/051743 discloses the use of water-soluble or water-dispersible copolymers of N-vinyllactam, vinyl acetate and polyethers as solubilizers for pharmaceutical, cosmetic, nutritional, agrochemical or other industrial uses. It is stated quite generally therein that the corresponding graft polymers can also be processed with the active ingredients in the melt.

WO 2009/013202 discloses that such graft polymers of N-vinyllactam, vinyl acetate and polyethers can be melted in an extruder and mixed with pulverulent or liquid active ingredients, and the extrusion described is at temperatures significantly below the melting point of the active ingredient.

However, extrusion is a complex process in apparatus terms. Moreover, extrusion can result in undesired thermal stresses on the feedstocks.

SUMMARY

One aspect of the present invention relates to pellets coated with active ingredient-containing coatings, wherein a sparingly water-soluble active ingredient is embedded in a coating composed of copolymers which are obtained by polymerizing vinyl acetate and N-vinyllactams in the presence of a polyether. Other aspects of the present invention relate to processes for producing such pellets and to the use thereof in pharmaceutical administration forms.

DETAILED DESCRIPTION

In accordance with one or more embodiments of the present invention, provided is a simpler process for incorporation of sparingly water-soluble substances into a formulation with improved solubility.

Accordingly, a formulation of sparingly water-soluble active ingredients has been found, which consist of carrier particles provided with active ingredient-containing coatings, the sparingly soluble active ingredients being embedded in coatings composed of amphiphilic copolymers.

The amphiphilic copolymers are obtained by free-radically initiated polymerization of a mixture of
 i) 30 to 80% by weight of N-vinyllactam,
 ii) 10 to 50% by weight of vinyl acetate and
 iii) 10 to 50% by weight of a polyether,
with the proviso that the sum of i), ii) and iii) is 100% by weight.

In addition, a process has been found for producing such formulations, which comprises producing the formulations by spraying a solution comprising one or more active ingredients and an amphiphilic copolymer onto a fluidized bed composed of carrier particles.

In one embodiment of the invention, preferred copolymers obtained from:
 i) 30 to 70% by weight of N-vinyllactam
 ii) 15 to 35% by weight of vinyl acetate and
 iii) 10 to 35% by weight of a polyether are used.

Polymers used with particular preference are obtainable from:
 i) 40 to 60% by weight of N-vinyllactam
 ii) 15 to 35% by weight of vinyl acetate and
 iii) 10 to 30% by weight of a polyether.

Polymers used with very particular preference are obtainable from:
 i) 50 to 60% by weight of N-vinyllactam
 ii) 25 to 35% by weight of vinyl acetate and
 iii) 10 to 20% by weight of a polyether.

For the preferred and particularly preferred compositions too, the proviso applies that the sum of components i), ii), and iii) is 100% by weight.

Useful N-vinyllactams are N-vinylcaprolactam or N-vinylpyrrolidone, or mixtures thereof. Preference is given to using N-vinylcaprolactam.

The graft bases used are polyethers. Useful polyethers are preferably polyalkylene glycols. The polyalkylene glycols may have molecular weights of 1000 to 100 000 Da [daltons], preferably 1500 to 35 000 Da, more preferably 1500 to 10 000 Da. The molecular weights are determined proceeding from the OH number measured to DIN 53240.

The glass transition temperatures are in the range from 40 to 120° C.

Particularly preferred polyalkylene glycols are polyethylene glycols. Additionally suitable are also polypropylene glycols, polytetrahydrofurans or polybutylene glycols which are obtained from 2-ethyloxirane or 2,3-dimethyloxirane.

Suitable polyethers are also random or block copolymers of polyalkylene glycols obtained from ethylene oxide, propylene oxide and butylene oxides, for example polyethylene glycol-polypropylene glycol block copolymers. The block copolymers may be of the AB or of the ABA type.

The preferred polyalkylene glycols also include those which are alkylated on one or both OH end groups. Useful alkyl radicals include branched or unbranched $C_1$- to $C_{22}$-alkyl radicals, preferably $C_1$-$C_{18}$-alkyl radicals, for example methyl, ethyl, n-butyl, isobutyl, pentyl, hexyl, octyl, nonyl, decyl, dodecyl, tridecyl or octadecyl radicals.

General processes for preparing the inventive copolymers are known per se. They are prepared by free-radically initiated polymerization, preferably in solution, in nonaqueous organic solvents or in mixed nonaqueous/aqueous solvents. Suitable preparation processes are described, for example, in WO 2007/051743 and WO 2009/013202, the disclosure of which regarding the preparation process is explicitly incorporated by reference.

It is a feature of the process that carrier particles are laden in standard fluidized bed units with a coating comprising sparingly soluble active ingredients.

This involves dissolving the active ingredient together with a suitable polymer in an organic solvent and spraying it onto the carrier particles.

Suitable carrier particles are spherical or at least approximately spherical particles, known as "nonpareils". In one embodiment of the invention, the nonpareils consist entirely, i.e. to an extent of 100% by weight, of pharmaceutical excipients. The nonpareils may consist of customary pharmaceutical excipients, for example sucrose, carrageenan, starch or microcrystalline cellulose. They are available in different sizes (100-2000 μm).

The solvents used may be all solvents in which the active ingredients are sufficiently soluble and which are vaporizable at standard pressure up to 160° C. Such solvents are: for example ethanol, methanol, isopropanol, acetone, ethyl acetate, dichloromethane, chloroform, dimethylformamide, methyl ethyl ketone.

Typically, the concentration of the polymer used in accordance with the invention in the solution is 1 to 40% by weight.

Typically, the ratio of active ingredient to amphiphilic polymer is between 1:99 and 80:20, preferably between 10:90 and 60:40. This results, in the final dried polymer coating of the pellets, in active ingredient concentrations of 1 to 80%.

The application can of course also be effected under protective gas (nitrogen). However, the use of the standard organic solvents without protective gas requires fluidized bed units with explosion-proof design. In addition, the process can be performed both with customary top-spray and rotor systems, and also in systems with a Wurster insert. A particularly suitable method of applying the formulations described is what is known as the jet fluidized bed (Procell technology).

In addition to the fluidized bed units, it is also possible to use other equipment in which the pellets are set in motion by rotation of tanks or by air flowing in, for example coating pans, horizontal drum coaters, Kugelcoaters, Innojet units.

The feed air temperatures are typically between 30 and 200° C., preferably between 40 and 120° C. The product temperatures are generally between 25 and 100° C., preferably between 30 and 80° C.

In a preferred embodiment, nonpareils are not used as carrier particles, but rather particles with the same or at least a similar composition as the coating, specifically comprising active ingredient and amphiphilic copolymer. These starter particles may have been produced by another process, for example by granulation or extrusion. However, they may also have been obtained by the same process. When this initial charge is only used in a small amount at the start—effectively as starter particles in order that the process can be started and larger particles are present, onto which the spray solution can be sprayed—particles which consist almost only of solid solution form in the course of the process.

The layer thickness of the active ingredient-containing coatings of amphiphilic polymer may be 5 to 1000 μm, preferably 10 to 700 μm.

It is of course possible to add further pharmaceutically customary excipients to the inventive formulation, for example further solubilizers, polymers, dyes, inorganic carriers, disintegrants, gel formers, retardants. The incorporation of gastric juice-resistant polymers or of retarding polymers allows the release of the active ingredient to be controlled.

The addition of crystallization-inhibiting substances, for example Kollidon 30, allows the stability of the solid solutions to be increased.

The formulations obtained by the process according to the invention can in principle be used in all fields in which only sparingly water-soluble or water-insoluble substances are either to be used in aqueous formulations or are to display their action in an aqueous medium.

According to the invention, the term "sparingly water-soluble" also comprises virtually insoluble substances and means that, for a solution of the substance in water at 20° C. at least 30 to 100 g of water is required per g of substance. In the case of virtually insoluble substances, at least 10 000 g of water are required per g of substance.

In the context of the present invention, sparingly-water soluble substances are preferably understood to mean biologically active substances such as active pharmaceutical ingredients for humans and animals, active cosmetic or agrochemical ingredients, or food supplements or active dietetic ingredients.

In addition, useful sparingly soluble substances to be solubilized also include dyes such as inorganic or organic pigments.

According to the invention, useful biologically active substances include, in principle, all solid active ingredients which have a melting point below the decomposition point under extrusion conditions of the copolymers. The copolymers can generally be extruded at temperatures up to 260° C. The lower temperature limit is guided by the composition of the mixtures to be extruded and the sparingly soluble substances to be processed in each case.

The active pharmaceutical ingredients used are water-insoluble substances or substances with low water solubility. According to DAB 9 (Deutsches Arzneimittelbuch, German Pharmacopeia), the solubility of active pharmaceutical ingredients is classified as follows: low solubility (soluble in 30 to 100 parts of solvent); sparingly soluble (soluble in 100 to 1000 parts of solvent); virtually insoluble (soluble in more than 10 000 parts of solvent). The active ingredients may come from any indication sector.

Examples here include benzodiazepines, antihypertensives, vitamins, cytostatics—especially taxol, anesthetics, neuroleptics, antidepressives, antivirals, for example anti-HIV drugs, antibiotics, antimycotics, antidementives, fungicides, chemotherapeutics, urologics, thrombocyte aggregation inhibitors, sulfonamides, spasmolytics, hormones, immunoglobulins, sera, thyroid therapeutics, psychopharmaceuticals, Parkinson's drugs and other antihyperkinetics, ophthalmics, neuropathy preparations, calcium metabolism regulators, muscle relaxants, anesthetics, lipid-lowering drugs, liver therapeutics, coronary drugs, cardiac drugs, immunotherapeutics, regulatory peptides and inhibitors thereof, hypnotics, sedatives, gynaecologicals, gout remedies, fibrinolytics, enzyme preparations and transport proteins, enzyme inhibitors, emetics, blood-flow stimulators, diuretics, diagnostics, corticoids, cholinergics, biliary therapeutics, antlasthmatics, bronchodilators, beta-receptor blockers, calcium antagonists, ACE inhibitors, arteriosclerotic drugs, anti-inflammation drugs, anticoagulants, antihypotensives, antihypoglycemics, antihypertensives, antifibrinolytics, antiepileptics, antiemetics, antidotes, antidiabetics, antiarrhythmics, antianemics, antiallergics, anthelmintics, analgesics, analeptics, aldosterone antagonists, slimming drugs.

Among the abovementioned pharmaceutical formulations, particular preference is given to those which are orally administrable formulations.

The content of inventive solubilizer in the pharmaceutical formulation is, depending on the active ingredient, in the range from 20 to 99% by weight.

A further particularly preferred embodiment relates to pharmaceutical formulations in which the active ingredients and the copolymer are present as a solid solution. In this case, the removal of the solvent and the incorporation of the active substance can be effected in one process step. The weight ratio of copolymer to active ingredient here is preferably from 1:1 to 4:1, but may be up to 100:1, especially up to 15:1. The only factors are that, when used in the finished drug form, a sufficient amount of active ingredient is firstly present in the drug form, and the forms secondly do not become too large in the case of oral drug forms.

To produce pharmaceutical administration forms, for example, tablets, the formulations obtained can be admixed with customary pharmaceutical excipients.

These are substances from the dais of the fillers, plasticizers, solubilizers, binders, silicates and disintegrants and adsorbents, lubricants, flow agents, dyes, stabilizers such as antioxidants, wetting agents, preservatives, mold release agents, aromas or sweeteners, preferably fillers, plasticizers and solubilizers.

The fillers added may, for example, be inorganic solids such as oxides of magnesium, aluminum, silicon, titanium carbonate or calcium carbonate, calcium phosphate or magnesium phosphate or organic fillers such as lactose, sucrose, sorbitol, mannitol.

Suitable plasticizers are, for example, triacetin, triethyl citrate, glyceryl monostearate, low molecular weight polyethylene glycols or poloxamers.

Suitable additional solubilizers are interface-active substances with an HLB (Hydrophilic Lipophilic Balance) value greater than 11, for example hydrogenated castor oil ethoxylated with 40 ethylene oxide units (Cremophor® RH 40), castor oil ethoxylated with 35 ethylene oxide units (Cremophor EL), Polysorbate 80, poloxamers or sodium laurylsulfate.

The lubricants used may be stearates of aluminum, calcium, magnesium and tin, and also magnesium silicate, silicones and the like.

The flow agents used may, for example, be talc or colloidal silicon dioxide.

A suitable binder is, for example, microcrystalline cellulose.

The disintegrants may be crosslinked polyvinylpyrrolidone or crosslinked sodium carboxymethyl starch. Stabilizers may be ascorbic acid or tocopherol.

Dyes are, for example, iron oxides, titanium dioxide, triphenylmethane dyes, azo dyes, quinoline dyes, indigotin dyes, carotenoids, in order to dye the administration forms, opacifiers, such as titanium dioxide or talc, in order to increase the transparency and to save dyes.

The formulations can, however, also be used in other dosage forms, such as in the form of capsule fillings or in sachets.

In addition to use in cosmetics and pharmacy, the formulations produced in accordance with the invention are also suitable for use in the foods sector, for example, for the incorporation of sparingly water-soluble or water-insoluble nutrients, assistants or additives, for example, fat-soluble vitamins or carotenoids. Examples include drinks colored with carotenoids.

The use of the formulations obtained in accordance with the invention in agrochemistry may comprise formulations which comprise pesticides, herbicides, fungicides or insecticides, and in particular also those formulations of crop protection compositions which are used as formulations for spraying or watering.

With the aid of the process according to the invention, it is possible to obtain active ingredient-containing coatings on nonpareils as so-called solid solutions comprising sparingly soluble substances. Solid solutions refer in accordance with the invention to systems in which no crystalline components of the sparingly soluble substance are observed.

On visual assessment of the stable solid solutions, no amorphous constituents are evident. The visual assessment can be effected with a light microscope either with or without a polarization filter at 40-fold magnification.

In addition, the formulations can also be examined for crystallinity or amorphicity with the aid of XRD (X-ray diffraction) and DSC (differential scanning calorimetry).

The formulations obtained by the process according to the invention are, as stated, present in amorphous form which means that the crystalline components of the biologically active substance are less than 5% by weight. The amorphous state is preferably checked by means of DSC or XRD. Such an amorphous state can also be referred to as an X-ray amorphous state.

The process according to the invention allows the production of stable formulations with a high active ingredient loading and good stability with regard to the amorphous state of the sparingly soluble substance.

The special feature of this process is that an amphiphilic polymer is used together with sparingly soluble active ingredients. The amphiphilic polymer is capable of keeping the active ingredient in dissolved form in the coating layer after removal of the solvent. The coating is thus not a customary pellet or tablet coating, but rather a coating which keeps sparingly soluble active ingredient in dissolved form. The advantage of solid solutions is that sparingly soluble active ingredients can better be made bioavailable thereby. The active ingredients may be present in the coating layer in amorphous form or in molecularly dissolved form.

A further advantage of this processing method is that solid solutions of sparingly soluble active ingredients can be processed to multiparticulate solid drug forms. These multiparticulate drug forms can be filled, for example, into hard gelatine capsules or even pressed to tablets.

Surprisingly, the polymer used as an amphiphilic polymer in accordance with the invention has excellent binding and film formation properties which are absolutely necessary for this application. Owing to the moderate spray-drying properties of the polymer used in accordance with the invention, this application, in which a solution likewise has to be atomized and dried and the particles additionally must not adhere to one another, was entirely unexpected.

EXAMPLES

Preparation of the Copolymer

In a stirred apparatus, the initial charge without the portion from feed 2 was heated to 77° C. under an N2 atmosphere. When the internal temperature of 77° C. had been attained the portion from feed 2 was added and partly polymerized for 15 min. Subsequently, feed 1 was metered in within 5 h and feed 2 within 2 h. Once all feeds had been metered in, the reaction mixture was polymerized for a further 3 h. After the further polymerization, the solution was adjusted to a solids content of 50% by weight.

Initial Charge:
  25 g of ethyl acetate
  104.0 g PEG 6000,
  1.0 g of feed 2
Feed 1:
  240 g of vinyl acetate
  456 g of vinylcaprolactam
  240 g of ethyl acetate
Feed 2:
  10.44 g of tert-butyl perpivalate (75% by weight in aliphatic mixture)
  67.90 g of ethyl acetate Subsequently, the solvent was removed by a spray process to obtain a pulverulent product. The K value was 36, measured in 1% by weight solution in ethanol in. The glass transition temperature was 70° C.

The twin screw extruder which was used for the production of the formulations described in the examples which follow had a screw diameter of 16 mm and a length of 40 D. The entire extruder was formed from 8 individually temperature-controllable barrel blocks. For the purpose of better material intake, the temperatures of the first two barrels were controlled at 20° C. and at 70° C. respectively. From the third barrel, a constant temperature was established.

The solid solutions produced were examined by means of XRD and DSC for crystallinity and amorphicity using the following equipment and conditions:

XRD
Instrument: D 8 Advance diffractometer with 9-tube sample changer (from Bruker/AXS)
Measurement method: θ-θ geometry in reflection
Angle range 2 Theta: 2-80°
Step width: 0.02°
Measurement time per angle step: 4.8 s
Divergence slit: Göbel mirror with 0.4 mm inserted aperture
Antiscattering slit: Soller slit
Detector: Sol-X detector
Temperature: Room temperature
Generator setting: 40 kV/50 mA
DSC
DSC Q 2000 from TA Instruments
Parameters:
Starting weight approx. 8.5 mg
Heating rate: 20K/min In the examples which follow, sucrose pellets with particle sizes of 710-850 μm (sieve fraction) were provided with active ingredient-containing coatings.

Example 1

| Composition    | Amount   |
| -------------- | -------- |
| Ethanol        | 1480 g   |
| Copolymer      | 80 g     |
| Carbamazepine  | 40 g     |
| Sucrose pellets | 1000 g  |

Glatt GPCG 3.1 Fluidized Bed Granulator:

| Process parameter          | Values |
| -------------------------- | ------ |
| Volume flow [m³/h]         | 140    |
| Feed air temperature [° C.] | 50     |
| Spray air pressure [bar]   | 1.5    |

The XRD analysis did not show any crystalline active ingredient fractions.

The release of the active ingredient from 518 mg pellets was carried out in a USP apparatus 2 in 700 ml of 0.1 normal HCl. After 60 minutes, 90% of the active ingredient had been released.

Example 2

| Composition    | Amount  |
| -------------- | ------- |
| Acetone        | 1600 g  |
| Copolymer      | 80 g    |
| Fenofibrate    | 40 g    |
| Sucrose pellets | 1000 g |

Glatt GPCG 3.1 Fluidized Bed Granulator

| Process parameter          | Values |
| -------------------------- | ------ |
| Volume flow [m³/h]         | 150    |
| Feed air temperature [° C.] | 40     |
| Spray air pressure [bar]   | 1.5    |

The XRD analysis did not show any crystalline active ingredient fractions.

The release of the active ingredient from 505 mg pellets was carried out in a USP apparatus 2 in 700 ml of 0.1 normal HCl. After 60 minutes, 100% of the active ingredient had been released.

Example 3

| Composition | Amount  |
| ----------- | ------- |
| Methanol    | 1485 g  |
| Copolymer   | 80 g    |
| Piroxicam   | 40 g    |
| MCC pellets | 1000 g  |

Glatt GPCG 3.1 Fluidized Bed Granulator

| Process parameter          | Values |
| -------------------------- | ------ |
| Volume flow [m³/h]         | 160    |
| Feed air temperature [° C.] | 65     |
| Spray air pressure [bar]   | 1.5    |

The XRD analysis did not show any crystalline active ingredient fractions.

The release of the active ingredient from 500 mg pellets was carried out in a USP apparatus 2 in 700 ml of 0.1 normal HCl. After 60 minutes, 100% of the active ingredient had been released.

Example 4

| Composition   | Amount  |
| ------------- | ------- |
| Acetone       | 1800 g  |
| Copolymer     | 90 g    |
| Griseofulvin  | 50 g    |
| Starch pellets | 1000 g |

Glatt GPCG 3.1 Fluidized Bed Granulator:

| Process parameter | Values |
|---|---|
| Volume flow [m³/h] | 160 |
| Feed air temperature [° C.] | 70 |
| Spray air pressure [bar] | 1.5 |

The XRD analysis did not show any crystalline active ingredient fractions.

The release of the active ingredient from 600 mg pellets was carried out in a USP apparatus 2 in 700 ml of 0.1 normal HCl. After 30 minutes, 100% of the active ingredient had been released.

Example 5

| Composition | Amount |
|---|---|
| Methanol | 1700 g |
| Copolymer | 130 g |
| Danazole | 60 g |
| Sucrose pellets | 1000 g |

Glatt GPCG 3.1 Fluidized Bed Granulator:

| Process parameter | Values |
|---|---|
| Volume flow [m³/h] | 160 |
| Feed air temperature [° C.] | 70 |
| Spray air pressure [bar] | 1.5 |

The XRD analysis did not show any crystalline active ingredient fractions.

The release of the active ingredient from 600 mg pellets was carried out in a USP apparatus 2 in 700 ml of 0.1 normal HCl. After 30 minutes, 100% of the active ingredient had been released.

Example 6

| Composition | Amount |
|---|---|
| Ethanol | 1600 g |
| Copolymer | 60 g |
| Carbamazepine | 60 g |
| Carrageenan pellets | 1000 g |

Glatt GPCG 3.1 Fluidized Bed Granulator:

| Process parameter | Values |
|---|---|
| Volume flow [m³/h] | 140 |
| Feed air temperature [° C.] | 50 |
| Spray air pressure [bar] | 1.5 |

The XRD analysis did not show any crystalline active ingredient fractions.

The release of the active ingredient from 500 mg pellets was carried out in a USP apparatus 2 in 700 ml of 0.1 normal HCl. After 120 minutes, 100% of the active ingredient had been released.

Example 7

| Composition | Amount |
|---|---|
| Methanol | 2800 g |
| Copolymer | 160 g |
| Ketoconazole | 80 g |
| Sucrose pellets | 1000 g |

Glatt GPCG 3.1 Fluidized Bed Granulator:

| Process parameter | Values |
|---|---|
| Volume flow [m³/h] | 150 |
| Feed air temperature [° C.] | 55 |
| Spray air pressure [bar] | 1.5 |

The XRD analysis did not show any crystalline active ingredient fractions.

The release of the active ingredient from 480 mg pellets was carried out in a USP apparatus 2 in 700 ml of 0.1 normal HCl. After 60 minutes, 100% of the active ingredient had been released.

Example 8

| Substance | Amount |
|---|---|
| Dichloromethane/Ethanol | 1520 g |
| Copolymer | 80 g |
| Itraconazole | 40 g |
| Sucrose pellets | 1000 g |

Glatt GPCG 3.1 Fluidized Bed Granulator:

| Process parameter | Values |
|---|---|
| Volume flow [m³/h] | 160 |
| Feed air temperature [° C.] | 65 |
| Spray air pressure [bar] | 1.5 |

The XRD analysis did not show any crystalline active ingredient fractions.

The release of the active ingredient from 520 mg pellets was carried out in a USP apparatus 2 in 700 ml of 0.1 normal HCl. After 80 minutes, 100% of the active ingredient had been released.

Example 9

| Substance | Amount |
|---|---|
| Methanol | 2000 g |
| Copolymer | 150 g |
| Piroxicam | 70 g |
| MCC pellets | 1000 g |

Glatt GPCG 3.1 fluidized bed granulator

| Process parameter | Values |
| --- | --- |
| Volume flow [m³/h] | 160 |
| Feed air temperature [° C.] | 65 |
| Spray air pressure [bar] | 1.5 |

The XRD analysis did not show any crystalline active ingredient fractions.

The release of the active ingredient from 500 mg pellets was carried out in a USP apparatus 2 in 700 ml of 0.1 normal HCl. After 60 minutes, 100% of the active ingredient had been released.

Example 10

| Substance | Amount |
| --- | --- |
| Acetone | 1000 g |
| Copolymer | 80 g |
| Fenofibrate | 20 g |
| Sucrose pellets | 1000 g |

Glatt GPCG 3.1 Fluidized Bed Granulator.

| Process parameter | Values |
| --- | --- |
| Volume flow [m³/h] | 152 |
| Feed air temperature [° C.] | 40 |
| Spray air pressure [bar] | 1.5 |

The XRD analysis did not show any crystalline active ingredient fractions.

The release of the active ingredient from 505 mg pellets was carried out in a USP apparatus 2 in 700 ml of 0.1 normal HCl. After 60 minutes, 100% of the active ingredient had been released.

Example 11

| Substance | Amount |
| --- | --- |
| Methanol | 3000 g |
| Copolymer | 200 g |
| Danazole | 85 g |
| MCC pellets | 1000 g |

Glatt GPCG 3.1 Fluidized Bed Granulator.

| Process parameter | Values |
| --- | --- |
| Volume flow [m³/h] | 160 |
| Feed air temperature [° C.] | 70 |
| Spray air pressure [bar] | 1.5 |

The XRD analysis did not show any crystalline active ingredient fractions.

The release of the active ingredient from 600 mg pellets was carried out in a USP apparatus 2 in 700 ml of 0.1 normal HCl. After 30 minutes, 100% of the active ingredient had been released.

Example 12

The starter particles used were ground solid solution (<500 μm extrudate) of copolymer and carbamazepine (composition 60:40).

Spray Solution:

| Substance | Amount |
| --- | --- |
| Ethanol | 3000 g |
| Copolymer | 180 g |
| Carbamazepine | 100 g |

ProCell 5 Spray Granulator:

| Process parameter | Values |
| --- | --- |
| Volume flow [m³/h] | 200 |
| Feed air temperature [° C.] | 50 |
| Spray air pressure [bar] | 1.5 |

The XRD analysis did not show any crystalline active ingredient fractions.

The release of the active ingredient from 518 mg pellets was carried out in a USP apparatus 2 in 700 ml of 0.1 normal HCl. After 90 minutes, 100% of the active ingredient had been released.

Example 13

The starter particles used were ground solid solution (<500 μm extrudate) of copolymer and danazole (composition 70:30).

Spray Solution:

| Substance | Amount |
| --- | --- |
| Methanol | 3000 g |
| Copolymer | 250 g |
| Danazole | 80 g |

ProCell 5 Spray Granulator:

| Process parameter | Values |
| --- | --- |
| Volume flow [m³/h] | 220 |
| Feed air temperature [° C.] | 60 |
| Spray air pressure [bar] | 1.5 |

The XRD analysis did not show any crystalline active ingredient fractions.

The release of the active ingredient from 518 mg pellets was carried out in a USP apparatus 2 in 700 ml of 0.1 normal HCl. After 45 minutes, 100% of the active ingredient had been released.

The invention claimed is:

1. A formulation of a sparingly water-soluble active ingredient, consisting of coated carrier particles, the coating comprising the sparingly water-soluble active ingredient, and amphiphilic copolymers,
   wherein the carrier particles have a different composition than the coating,
   wherein the sparingly water-soluble active ingredient is embedded in the coating, and wherein the amphiphilic copolymers are obtained by free-radically initiated polymerization of a mixture of:
i) 40 to 60% by weight of N-vinyllactam
ii) 15 to 35% by weight of vinyl acetate and
iii) 10 to 30% by weight of a polyether,
with the proviso that the sum of i), ii) and iii) is 100% by weight.

2. The formulation of claim 1, wherein the amphiphilic copolymers are obtained from: i) 50 to 60% by weight of N-vinyllactam ii) 25 to 35% by weight of vinyl acetate and iii) 10 to 20% by weight of a polyether.

3. The formulation of claim 1, wherein the carrier particles used are pellets containing pharmaceutical excipients.

4. The formulation of claim 1, wherein the carrier particles consist of sucrose, carrageenan, starch or microcrystalline cellulose.

5. The formulation of claim 1, wherein the carrier particles have particle sizes of 100 to 2000 .mu.m.

6. The formulation of claim 1, wherein the coating additionally comprises pharmaceutical excipients.

7. The formulation of claim 1, wherein the coatings comprise 20 to 99% by weight of amphiphilic polymer.

8. A process for producing formulations comprising spraying a solution comprising one or more active ingredients and an amphiphilic copolymer in an organic solvent onto a fluidized bed composed of carrier particles,
wherein the carrier particles have a different composition than the coating, and
wherein the amphiphilic copolymers are obtained by free-radically initiated polymerization of a mixture of
i) 50 to 60% by weight of N-vinyllactam
ii) 25 to 35% by weight of vinyl acetate and
iii) 10 to 20% by weight of a polyether,
with the proviso that the sum of i), ii) and iii) is 100% by weight.

9. The process of claim 8, wherein the organic solvent is vaporizable at temperatures less than 160° C. at standard pressure.

10. The process of claim 8, wherein the solvent used is ethanol, methanol, isopropanol, acetone, ethyl acetate, dichloromethane, chloroform, dimethylformamide, methyl ethyl ketone or mixtures thereof.

11. A dosage form comprising the formulation of claim 1.

12. The dosage form of claim 11, wherein the dosage form is in the form of tablets, capsules or sachets.

13. The process of claim 8, wherein the amphiphilic copolymers are obtained from:
i) 50 to 60% by weight of N-vinyllactam
ii) 25 to 35% by weight of vinyl acetate and
iii) 10 to 20% by weight of a polyether.

14. The process of claim 8, wherein the carrier particles have particle sizes of 100 to 2000 .mu.m.

* * * * *